(12) United States Patent
Shoji et al.

(10) Patent No.: US 8,008,357 B2
(45) Date of Patent: Aug. 30, 2011

(54) METHOD FOR CONTROLLING AVERAGE PORE DIAMETER OF POROUS BODY COMPRISING APATITE/COLLAGEN COMPOSITE FIBERS

(75) Inventors: Daisuke Shoji, Tokyo (JP); Katsumi Kawamura, Tokyo (JP); Takehiko Nakajima, Tokyo (JP); Junzo Tanaka, Ibaraki (JP); Masanori Kikuchi, Ibaraki (JP); Toshiyuki Ikoma, Ibaraki (JP); Naomi Mochizuki, Tokyo (JP)

(73) Assignees: Hoya Corporation, Tokyo (JP); National Institute for Materials Science, Ibaraki-Ken (JP)

( * ) Notice: Subject to any disclaimer, the term of this patent is extended or adjusted under 35 U.S.C. 154(b) by 45 days.

(21) Appl. No.: 10/599,435

(22) PCT Filed: Mar. 23, 2005

(86) PCT No.: PCT/JP2005/005271
§ 371 (c)(1),
(2), (4) Date: Dec. 12, 2006

(87) PCT Pub. No.: WO2005/097217
PCT Pub. Date: Oct. 20, 2005

(65) Prior Publication Data
US 2008/0234396 A1    Sep. 25, 2008

(30) Foreign Application Priority Data
Mar. 30, 2004    (JP) .................................. 2004-100765

(51) Int. Cl.
*A61K 38/17*    (2006.01)
(52) U.S. Cl. .................... 516/103; 424/422; 424/423
(58) Field of Classification Search .................... 516/103
See application file for complete search history.

(56) References Cited

U.S. PATENT DOCUMENTS

| | | | |
|---|---|---|---|
| 4,795,467 A | 1/1989 | Piez et al. | |
| 4,969,913 A | 11/1990 | Ojima | |
| 5,017,518 A | 5/1991 | Hirayama et al. | |
| 5,064,436 A | 11/1991 | Ogiso et al. | |
| 5,082,803 A | 1/1992 | Sumita | |
| 5,089,195 A | 2/1992 | Ichitsuka et al. | |
| 5,171,720 A | 12/1992 | Kawakami | |
| 5,215,941 A | 6/1993 | Yasukawa et al. | |
| 5,776,193 A | 7/1998 | Kwan et al. | |
| 6,187,046 B1 | 2/2001 | Yamamoto et al. | |
| 6,187,047 B1 | 2/2001 | Kwan et al. | |
| 6,203,574 B1 | 3/2001 | Kawamura | |
| 6,541,023 B1 | 4/2003 | Andre et al. | |
| 6,733,528 B2 | 5/2004 | Abe et al. | |
| 6,764,517 B2 | 7/2004 | Yamamoto et al. | |
| 6,902,584 B2 | 6/2005 | Kwan et al. | |
| 7,153,938 B2 | 12/2006 | Kikuchi et al. | |
| 2004/0096475 A1 | 5/2004 | Hiraida et al. | |
| 2004/0220680 A1 | 11/2004 | Yamamoto et al. | |
| 2005/0004242 A1 | 1/2005 | Sotome et al. | |
| 2005/0271695 A1 | 12/2005 | Kikuchi et al. | |
| 2006/0013894 A1 | 1/2006 | Yamamoto et al. | |
| 2006/0292350 A1 | 12/2006 | Kawamura et al. | |

FOREIGN PATENT DOCUMENTS

| | | |
|---|---|---|
| EP | 1500405 A1 | 1/1925 |
| EP | 1155705 | 11/2001 |
| JP | 2-265935 | 10/1990 |
| JP | 06-304242 | 11/1994 |
| JP | 11-192081 | 7/1999 |
| JP | 3048289 | 3/2000 |
| JP | 2003-190271 | 7/2003 |
| WO | 97/14376 | 4/1997 |
| WO | 01/92322 | 12/2001 |
| WO | 03/092759 | 11/2003 |
| WO | 2004/041320 | 5/2004 |
| WO | 2004-103422 | 12/2004 |
| WO | 2004/103422 | 12/2004 |

OTHER PUBLICATIONS

Chang, "Preparation of a porous hydroxyapatite/collagen nanocomposite using glutaraldehyde as a crosslinkage agent", Journal of Materials Science Letters 20, 2001, 1199-1201.*

Lee et al., "Characerization of UV-irradiated Dense/porous Collagen Membranes: Morphology, Enzymatic, Degradation, and Mechanical Properties", Yonsei Medical Journal, vol. 42, No. 2, pp. 172-179, 2001.*

Kikuchi et al. (Porous Body Preparation of Hydroxyapatite/Collagen Nanocomposites for Bone Tissue Regeneration, Key Engineering Materials, vols. 254-256 (2004), pp. 561-564).*

Kikuchi, M. et al., "Porous Body Preparation of Hydroxyapatite/Collagen Nanocomposites for Bone Tissue Regeneration," *Key Engineering Materials*, vols. 254-256, pp. 561-564 (2004).

Gelinsky, M. et al., "Porous Scaffolds Made From Mineralized Collagen—A Biomimetic Bone Graft Material," *Materialwissenschaft und Wekstoffiechnik*, vol. 35, No. 4, pp. 229-233 (2004).

Tateishi, T. et al., "Biodegradable Porous Scaffolds for Tissue Engineering," *Journal of Artificial Organs*, vol. 5, pp. 77-83 (2002).

Kang, H. et al., "Fabrication of Porous Gelatin Scaffolds for Tissue Engineering," *Biomaterials*, vol. 20, pp. 1339-1344 (1999).

von Heimburg, D. et al., "Human Preadipocytes Seeded on Freeze-Dried Collagen Scaffolds Investigated in Vitro and in Vivo," *Biomaterials*, vol. 22, pp. 429-438 (2001).

(Continued)

*Primary Examiner* — Milton I Cano
*Assistant Examiner* — Chun-Cheng Wang
(74) *Attorney, Agent, or Firm* — Greenblum & Bernstein, P.L.C.

(57) ABSTRACT

In the process of producing a porous body containing a fibrous apatite/collagen composite by gelating a dispersion comprising the fibrous apatite/collagen composite, collagen and water, freeze-drying the resultant gel to form a porous body, and cross-linking collagen in the porous body, a method for controlling the average pore diameter of the porous body by the solidification time of the gel in the freezing step.

2 Claims, 7 Drawing Sheets

OTHER PUBLICATIONS

Kato, R et al., "Preparation of Hydroxyapatite Ceramics with One-Dimensional Pores Using Freeze-dry Process," Dai 6 Kai Seitai Kanren Ceramics Toronkai Koen Yokosyu, p. 22 (2002).

Chang et al., "Preparation of a Porous Hydroxyapatite/Collagen Nanocomposite Using Glutaraldehyde as a Crosslinking Agent," J. Mat. Sci. Let., vol. 20, No. 13, pp. 1199-1201 (2001).

English language Abstract of WO 01/92322.
English language Abstract of JP 7-101708.
English language Abstract of JP 11-199209.
English language Abstract of JP 2000-005298.
English language Abstract of JP 11-192081.
English language Abstract of JP 2003-190271.

* cited by examiner

METHOD FOR CONTROLLING AVERAGE PORE DIAMETER OF POROUS BODY COMPRISING APATITE/COLLAGEN COMPOSITE FIBERS

FIELD OF THE INVENTION

The present invention relates to a porous body containing a fibrous apatite/collagen composite (hereinafter referred to simply as "apatite/collagen porous body") suitable for artificial bone, cell scaffolds, etc., particularly to a method for controlling the average pore diameter of the apatite/collagen porous body.

BACKGROUND OF THE INVENTION

Because of excellent compatibility with human bone, artificial bone made of apatite can be bonded to the human bone directly. Accordingly, the artificial bone made of apatite has recently been appreciated for effectiveness, finding clinical applications in cosmetic surgery, neurosurgery, plastic surgery, oral surgery, etc. However, artificial ceramic bone such as apatite is not necessarily completely identical with human bone in terms of mechanical properties and physiological properties. For instance, a so-called artificial ceramic bone made only of apatite is harder and more brittle than the human bone. While the human bone is repeatedly subjected to metabolism of absorption and regeneration, the artificial bone made of apatite is not substantially dissolved but semi-permanently remains in human body. The remaining artificial bone breaks human bone at an interface with the human bone, making it likely to cause bone fracture.

Research has recently become active on artificial bone decomposable in the human body, which is closer in composition to human bone than the artificial apatite bone, and various proposals have been made. For instance, JP 11-513590 A discloses a porous body having a network structure, in which collagen and, if necessary, other binders are bonded to hydroxyapatite. Because this porous body is biodecomposable, human bone is formed in the porous body, and the porous body per se is absorbed in a human body. Accordingly, this porous body can be used for the fixation of vertebra, the filling of bone defects, the repair of fractured bone and, the grafting of periodontal defects, etc.

Because mechanical strength and biocompatibility are substantially inversely proportional to each other in porous bodies comprising apatite and collagen, larger mechanical strength tends to be accompanied by smaller biocompatibility. The porous bodies are thus designed such that these properties are balanced for particular applications. The properties of porous bodies comprising apatite and collagen depend on their porosities to some extent, and the porosity of a porous body can be controlled by the percentage of a liquid (water, an aqueous phosphoric acid solution, etc.), etc. in starting materials. However, because artificial bone usable for various applications should have different properties depending on the applications, the control of porosity is not sufficient.

It is known that mechanical strength and biocompatibility depend not only on the porosity of porous bodies comprising apatite and collagen, but also on their average pore diameters. For instance, the larger average pore diameter the porous body has, the more easily a body fluid, tissues, etc. enter into the pores of the porous body embedded in a human body, and thus the larger biocompatibility the porous body has. The average pore diameter is a factor having large influence on the properties of the porous body comprising apatite and collagen, and there is increasingly larger demand to provide porous bodies with desired average pore diameters recently. However, methods for producing porous bodies comprising apatite and collagen with their average pore diameters controlled have not been known yet.

OBJECT OF THE INVENTION

Accordingly, an object of the present invention is to provide a method for controlling the average pore diameter of an apatite/collagen porous body in its production process.

DISCLOSURE OF THE INVENTION

As a result of intense research in view of the above object, the inventors have found that an apatite/collagen porous body obtained by freeze-drying a gel comprising a fibrous apatite/collagen composite and collagen, and cross-linking the resultant porous body has an average pore diameter, which depends on the time for freezing the gel. The present invention has been completed based on this finding.

Thus, in the production process of an apatite/collagen porous body comprising gelating a dispersion comprising a fibrous apatite/collagen composite, collagen and water, freeze-drying the resultant gel to form a porous body, and cross-linking collagen in the porous body, the present invention provides a method for controlling the average pore diameter of the apatite/collagen porous body by the solidification time of the gel in the freezing step.

The solidification time of the gel is preferably controlled by a temperature at which the gel is kept for freezing. The temperature at which the gel is kept for freezing is preferably −100° C. to 0° C., more preferably −90° C. to 0° C., particularly substantially constant between −80° C. and −20° C.

DESCRIPTION OF THE BEST MODE OF THE INVENTION

Figure 1:
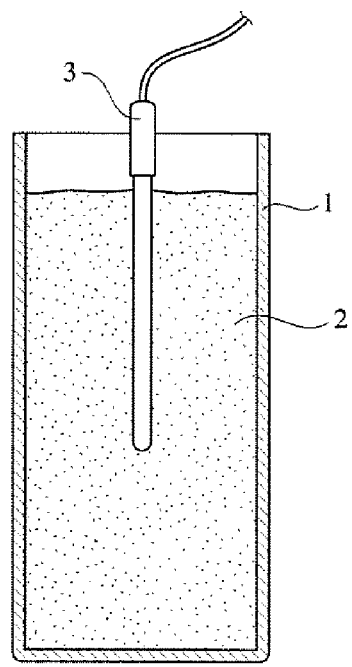
FIG. 1 is a cross-sectional view showing a gel, into which a temperature sensor is inserted.

In the production of a porous body comprising a fibrous apatite/collagen composite by gelating a dispersion containing the fibrous apatite/collagen composite and collagen as a binder and freezing the resultant gel to cross-link the collagen, the method of the present invention controls the average pore diameter of the apatite/collagen porous body to a desired level by means of the time for freezing the gel. The production method of the apatite/collagen porous body will be explained first, and the control of the average pore diameter in the gel-freezing step will then be explained.

[1] Production Method of Porous Body Containing Fibrous Apatite/Collagen Composite (1) Fibrous Apatite/Collagen Composite (a) Starting Material The fibrous apatite/collagen composite is produced from collagen, phosphonic acid and its salts, and calcium salts, as starting materials. Though not particularly restricted, the collagen may be extracted from animals, etc. The kinds, parts, ages, etc. of the animals are not particularly restrictive. In general, collagen obtained from skins, bones, cartilages, tendons, internal organs, etc. of mammals such as cow, pig, horse, rabbit and rat, and birds such as hen, etc. may be used. Collagen-like proteins obtained from skins, bones, cartilages, fins, scales, internal organs, etc. of fish such as cod, flounder, flatfish, salmon, trout, tuna, mackerel, red snapper, sardine, shark, etc. may also be used. The extraction method of collagen is not particularly restrictive but may be a usual one. In place of collagen extracted from animal tissues, collagen produced by gene recombination technologies may also be used.

Phosphoric acid and its salts [hereinafter referred to simply as "phosphoric acid (salt)"] include phosphoric acid, disodium hydrogenphosphate, sodium dihydrogenphosphate, dipotassium hydrogenphosphate, potassium dihydrogenphosphate, etc. The calcium salts include calcium carbonate, calcium acetate, and calcium hydroxide. The phosphate and the calcium salt are preferably added in the form of a uniform aqueous solution or suspension.

The apatite/collagen mass ratio of the product can be controlled by a mass ratio of the apatite-forming materials [phosphoric acid (salt) and calcium salt] and collagen used. Accordingly, the mass ratio of the apatite-forming materials and collagen used is properly determined depending on a targeted composition ratio of the fibrous apatite/collagen composite. A ratio of apatite to collagen in the fibrous apatite/collagen composite is preferably 9/1 to 6/4, for instance, 8/2.

(b) Preparation of Solution

First, an aqueous phosphoric acid (salt) solution and an aqueous calcium salt solution are prepared. Though the concentrations of the aqueous phosphoric acid (salt) solution and the aqueous calcium salt solution are not particularly restrictive as long as the phosphoric acid (salt) and the calcium salt are at a desired ratio, it is preferable for the convenience of a dropping operation described later that the concentration of the aqueous phosphoric acid (salt) solution is about 50-250 mM, and that the concentration of the aqueous calcium salt solution is about 200-600 mM. Collagen is added to the above-described aqueous phosphoric acid (salt) solution generally in the form of an aqueous solution in phosphoric acid. An aqueous solution of collagen in phosphoric acid may contain collagen at a concentration of about 0.5-1% by mass, and phosphoric acid at a concentration of about 10-30 mM. For practical purposes, the concentration of collagen is 0.8-0.9% by mass, for instance, 0.85% by mass, and the concentration of phosphoric acid is about 15-25 mM, for instance, 20 mM.

(c) Production of Fibrous Apatite/Collagen Composite

Water substantially in the same amount as that of the aqueous calcium salt solution to be added is charged into a reactor and heated to about 40° C. in advance. An aqueous phosphoric acid (salt) solution containing collagen and an aqueous calcium salt solution are simultaneously dropped thereinto. The length of the synthesized fibrous apatite/collagen composite can be controlled by adjusting dropping conditions. The aqueous solution of collagen in phosphoric acid (salt) and the aqueous calcium salt solution are simultaneously dropped preferably at a speed of about 10-50 ml/min. The reaction solution is preferably stirred at about 50-300 rpm. During the dropping, it is preferable to keep the concentrations of calcium and phosphoric acid ions in the reaction solution to 3.75 mM or less and 2.25 mM or less, respectively. With the calcium and phosphoric acid ions kept in these concentration ranges, the reaction solution is kept at pH of 8.9-9.1. Outside the above concentration ranges of calcium and/or phosphoric acid ions, the self-organization of the composite is hindered. The term "self-organization" used herein means that hydroxyapatite (calcium phosphate having an apatite structure) has orientation peculiar to living bone along collagen fibers, namely that the C-axis of the hydroxyapatite is in alignment with the collagen fibers. The above dropping conditions provide a self-organized, fibrous apatite/collagen composite as long as 1 mm or less, preferable as a starting material for the porous body.

After the completion of dropping, a slurry-like mixture of the fibrous apatite/collagen composite and water is freeze-dried. The freeze-drying can be carried out by rapid drying in vacuum in a frozen state at $-10°$ C. or lower.

(2) Preparation of Dispersion Containing Fibrous Apatite/Collagen Composite

The fibrous apatite/collagen composite is mixed with a liquid such as water, an aqueous phosphoric acid solution, etc., and stirred to prepare a paste-like dispersion. The amount of the liquid is determined such that the percentage of the liquid in the dispersion containing the fibrous apatite/collagen composite is preferably 80 to 99% by volume, more preferably 90 to 97% by volume. The resultant porous body has porosity P, which depends on a volume ratio of the fibrous apatite/collagen composite to the liquid in the dispersion as represented by the following formula (1):

$$P = X/(X+Y) \qquad (1),$$

wherein X represents the volume of the fibrous apatite/collagen composite in the dispersion, and Y represents the volume of the liquid in the dispersion. Accordingly, it is possible to control the porosity P of the porous body by adjusting the amount of the liquid to be added. After adding the liquid, the resultant dispersion is preferably stirred. The fibrous apatite/collagen composite can be cut to a wider fiber length distribution by sufficiently stirring the dispersion, thereby providing the resultant porous body with improved strength.

The composite dispersion is mixed with collagen as a binder and further stirred. The amount of collagen added is preferably 1 to 10% by mass, more preferably 3 to 6% by mass, based on 100% by mass of the fibrous apatite/collagen composite. Like the composite, collagen is preferably added in the form of an aqueous solution in phosphoric acid. Though the concentration, etc. of the aqueous solution of collagen in phosphoric acid is not particularly restrictive, the concentration of collagen is 0.8-0.9% by mass, for instance, 0.85% by mass, and the concentration of phosphoric acid is 15-25 mM, for instance, 20 mM, from the practical point of view.

(3) Gelation of Dispersion

Because the addition of an aqueous solution of collagen in phosphoric acid (salt) turns the dispersion acidic, a sodium hydroxide solution is added until the dispersion has pH of about 7. The pH of the dispersion is preferably 6.8 to 7.6, more preferably 7.0 to 7.4. By adjusting the pH of the dispersion to 6.8 to 7.6, it is possible to accelerate to turn the collagen added as a binder fibrous.

The dispersion is mixed with an about 2.5-10-times concentrated solution of a physiological buffer saline (PBS) of phosphoric acid and stirred to adjust the ionic strength of the dispersion to 0.2 to 0.8. The more preferred ionic strength is on the same level (about 0.2-0.8) as that of PBS. Increase in the ionic strength of the dispersion can accelerate collagen added as a binder to form fibers.

The dispersion charged into a molding die is kept at a temperature of 35° C. to 43° C. for gelation. With the dispersion kept at 35° C. to 43° C., the collagen added as a binder forms fibers, thereby turning the dispersion to a gel. The heating temperature is more preferably 35° C. to 40° C. For sufficient gelation of the dispersion, the heating time is preferably 0.5 to 3.5 hours, more preferably 1 to 3 hours. The gelled dispersion can prevent the fibrous apatite/collagen composite from precipitating therein, thereby producing a uniform porous body. The gelled dispersion is in a jelly-like state.

(4) Freeze-Drying of Gel

The gel containing the fibrous apatite/collagen composite is frozen in a freezer. The average pore diameter of the resultant apatite/collagen porous body depends on the gel-freezing time. The control method of the average pore diameter will be explained in detail later. The temperature in the freezer is preferably −100° C. to 0° C., more preferably −100° C. to −10° C., particularly −80° C. to −20° C. When it is lower than −100° C., the resultant apatite/collagen porous body has too small an average pore diameter. When it is higher than 0° C., the gel is not frozen, or freezing takes too much time, resulting in a porous body with too large an average pore diameter.

The solidified gel is freeze-dried to a porous body. The freeze-drying is conducted by evacuating the frozen gel at −10° C. or lower, and rapidly drying it, as in the case of the fibrous apatite/collagen composite. The freeze-drying need only be conducted until the dispersion is fully dried, so the freezing time is not particularly restricted, but it is generally about 24-72 hours.

(5) Cross-Linking of Collagen

The cross-linking of collagen may be carried out by any methods such as physical cross-linking methods using γ-rays, ultraviolet rays, electron beams, thermal dehydration, etc., or chemical cross-linking methods using cross-linking agents, condensation agents, etc. In the case of the chemical cross-linking, the freeze-dried porous body is immersed in a cross-linking agent solution to cross-link collagen in the porous body. The cross-linking agents may be, for instance, aldehydes such as glutaraldehyde, formaldehyde, etc.; isocyanates such as hexamethylene diisocyanate, etc.; carbodiimides such as a hydrochloric acid salt of 1-ethyl-3-(3-dimethylaminopropyl)carbodiimide; polyepoxies such as ethylene glycol diethyl ether, etc.; transglutaminase, etc. Among these cross-linking agents, glutaraldehyde is particularly preferable from the aspects of the easiness of controlling the degree of cross-linking and the biocompatibility of the resultant porous body.

When cross-linking is conducted by using glutaraldehyde, the concentration of a glutaraldehyde solution is preferably 0.005 to 0.015% by mass, more preferably 0.005 to 0.01% by mass. The porous body should be dehydrated. When alcohol such as ethanol, etc. is used as a solvent for the glutaraldehyde solution, the dehydration of the porous body can be conducted simultaneously with the cross-linking of collagen. A cross-linking reaction occurs in a state where the fibrous apatite/collagen composite is contracted, by conducting the dehydration and the cross-linking simultaneously, so that the resultant porous body can have improved elasticity.

After the cross-linking, the porous body is immersed in an aqueous solution of about 2% by mass of glycine to remove unreacted glutaraldehyde, and then washed with water. The porous body is further immersed in ethanol for dehydration, and then dried at room temperature.

In the case of cross-linking by thermal dehydration, the freeze-dried porous body may be kept at 100° C. to 160° C. and 0-100 hPa for 10-12 hours in a vacuum oven.

[2] Method for Controlling Average Pore Diameter of Porous Body Containing Fibrous Apatite/Collagen Composite The average pore diameter of the apatite/collagen porous body depends on the freezing time of the gel containing a fibrous apatite/collagen composite. Accordingly, to control the average pore diameter, it is necessary to investigate in advance the relation between the gel-freezing conditions (freezing-environment temperature and solidification time), and the average pore diameter of the resultant apatite/collagen porous body.

(1) Freezing-Environment Temperature to and Solidification Time Sb

Figure 2:
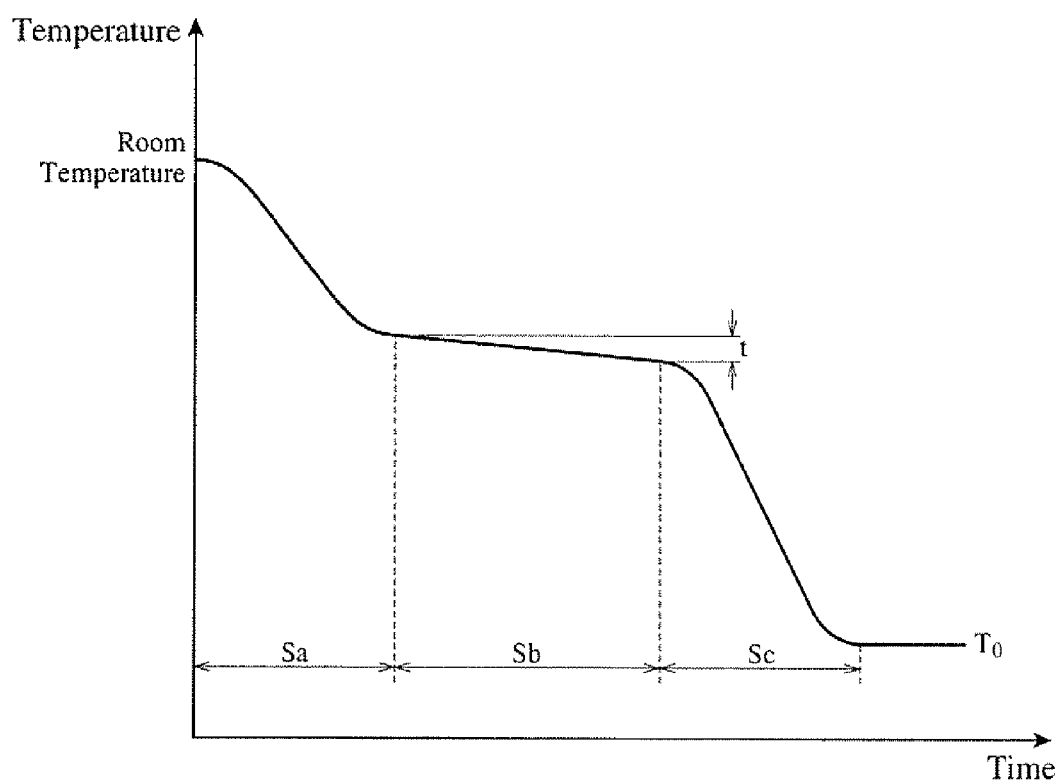
FIG. 2 is a graph schematically showing the temperature change of a porous body in the freezing step.

As shown in FIG. 1, a temperature sensor 3 is inserted into the gel 2 in its center in a cylindrical molding die 1. This molding die 1 is held in a freezer until the gel 2 is solidified. FIG. 2 is a graph schematically showing the temperature change with time of the gel in the freezer. The freezer temperature is set at $T_0$ (° C.).

As shown in FIG. 2, the temperature of the gel placed in the freezer is rapidly lowered from room temperature (period Sa), and becomes constant or is slowly lowered when it reaches a certain level (period Sb). Thus, the gel is solidified while the temperature of the gel is constant or slowly lowering. The time period during which the temperature is constant or slowly lowering in the solidification of the gel is defined herein as "solidification time (Sb)," and the temperature (t ° C.) in that time period is defined as "solidification temperature." Also, the temperature of an environment in which the gel is kept for freezing (for instance, the temperature of a freezer) is defined as "freezing-environment temperature $T_0$." After completely solidified, the temperature of the gel is lowered to the freezing-environment temperature $T_0$ (Sc).

The solidification time Sb is controlled by the freezing-environment temperature $T_0$. In the case of a cylindrical gel of 1-2 cm in diameter and 3-5 cm in height, for instance, the solidification time Sb is 300-500 seconds at a freezing-environment temperature $T_0$ of −80° C., and 3000-3500 seconds at a freezing-environment temperature $T_0$ of −20° C. Although the freezing-environment temperature $T_0$ may not be constant, the solidification time Sb can easily be controlled when the temperature change is kept within ±5° C.

Figure 3:
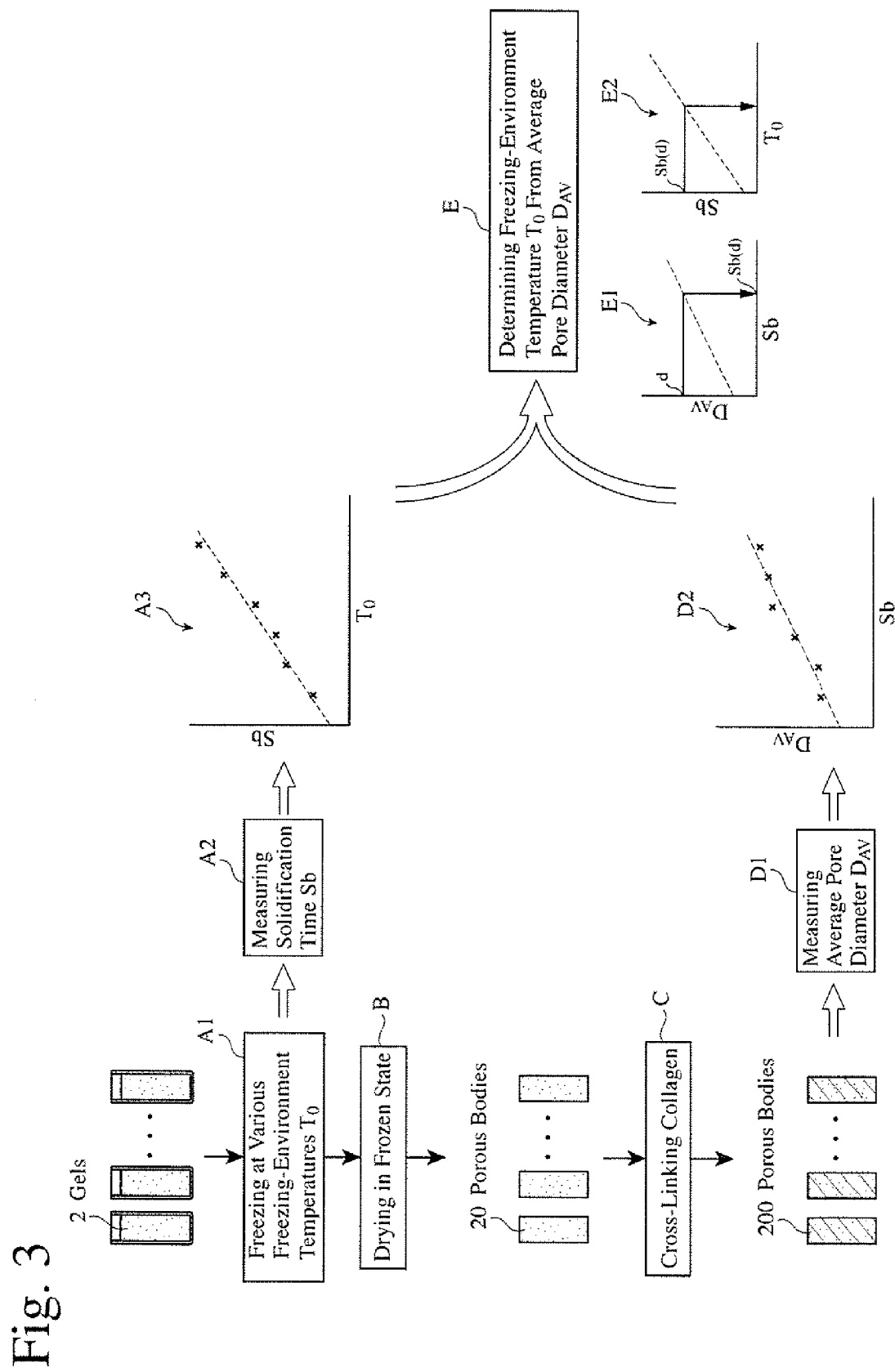
FIG. 3 is a flow chart showing a method for controlling the average pore diameter of an apatite/collagen porous body according to the present invention.

As shown in FIG. 3, pluralities of gels 2 are frozen at various freezing-environment temperatures $T_0$ (step A1), and the solidification time Sb of each gel 2 is measured (step A2) to prepare a graph showing the relation between the freezing-environment temperature $T_0$ and the solidification time Sb (step A3). The solidification time Sb is substantially proportional to the freezing-environment temperature $T_0$. In the example shown in FIG. 3, the solidification time Sb changes linearly relative to the freezing-environment temperature $T_0$, though it may change along a curve depending on the shape and composition of the gel 2. To secure reliability, the solidification time Sb is preferably measured at three or more freezing-environment temperatures $T_0$ and plotted in a graph. When the solidification time Sb changes along a curved line in the graph, it is preferably measured at four or more freezing-environment temperatures $T_0$.

(2) Solidification Time Sb and Average Pore Diameter

After collagen is cross-linked in the porous body 20 obtained by freeze-drying (step B) in the step C, the average pore diameter $D_{AV}$ of the resultant porous body 200 is measured (step D1). The diameters of three pores within 10 mm from the temperature sensor 3 are preferably measured to determine their average. By measuring the average pore diameters $D_{AV}$ of the apatite/collagen porous bodies 200 obtained at various lengths of solidification time Sb, the relation between the solidification time Sb and the average pore diameter $D_{AV}$ can be plotted on a graph (step D2). The average pore diameter $D_{AV}$ of the porous body can be determined by a line-intercept method. Specifically, a polished surface of the porous body 200 is photographed by an electron microscope, and straight lines are drawn on the resultant photograph. The inner diameters of all pores through which the straight lines pass are measured and averaged. The average pore diameter is substantially proportional to the solidification time Sb; the shorter the solidification time Sb, the smaller the average pore diameter and vice versa. In the example shown in FIG. 3, a line showing the relation of the average pore diameter $D_{AV}$ to the solidification time Sb is straight, but it may be curved.

(3) Method for Controlling Average Pore Diameter

By using a graph showing the relation between the solidification time Sb and the average pore diameter $D_{AV}$ (step D2) and a graph showing the relation between the freezing-environment temperature $T_0$ and the solidification time Sb (step A3), the freezing-environment temperature $T_0$ for producing the apatite/collagen porous body having a desired average pore diameter can be determined. For instance, to produce the apatite/collagen porous body having an average pore diameter d μm, the solidification time Sb(d) for providing the average pore diameter d μm is determined from a graph of the solidification time Sb and the average pore diameter $D_{AV}$ (step E1), and the freezing-environment temperature $T_0$ for achieving the solidification time Sb(d) is determined from a graph of the freezing-environment temperature $T_0$ and the solidification time Sb (step E2). Thus, the freezing-environment temperature $T_0$ of a gel for producing the apatite/collagen porous body having a desired average pore diameter can be determined (step E).

For instance, when a cylindrical porous body having a diameter of 1-2 cm is produced, the solidification time Sb should be 450-500 seconds to achieve the average pore diameter of 100 μm. Thus, the freezing-environment temperature $T_0$ is set at −85° C. to −75° C. Also, because the solidification time Sb should be 2700-3000 seconds to achieve the average pore diameter of 350 μm, the freezing-environment temperature $T_0$ may be set at −40° C. to −30° C. Thus, the solidification time Sb is adjusted to 200-3500 seconds by setting the freezing-environment temperature $T_0$ at −80° C. to −10° C., so that the porous body can be provided with an average pore diameter of 50-500 μm.

The present invention will be explained in more detail with reference to Examples below without intention of restricting the scope of the present invention.

EXAMPLE 1

(1) Production of Fibrous Apatite/Collagen Composite 412 g of an aqueous solution of collagen in phosphoric acid (concentration: 0.97% by weight, phosphoric acid: 20 mM) was added to 400 ml of a 120-mM aqueous phosphoric acid solution and stirred to prepare a solution I. 400 ml of a 400-mM calcium hydroxide solution (solution II) was also prepared. After 200 ml of pure water was charged into a reactor, the solutions I and II were simultaneously dropped thereinto. During dropping, a reaction solution was stirred, and the dropping speeds of the solutions I and II were controlled to keep the reaction solution at pH of 8.9-9.1. The resultant fibrous apatite/collagen composite was as long as about 1-2 mm. A slurry of fibrous apatite/collagen composite was freeze-dried. The apatite/collagen ratio of the fibrous apatite/collagen composite was 8/2 by mass.

(2) Production of Porous Body (a-1) Containing Fibrous Apatite/Collagen Composite After 4.84 ml of pure water was added to 2 g of the dried fibrous apatite/collagen composite, 0.06 ml of a 1-N aqueous NaOH solution was added thereto and stirred. After the resultant fibrous apatite/collagen composite slurry was mixed with 2 g of an aqueous solution of collagen in phosphoric acid (concentration: 0.97% by weight, phosphoric acid: 20 mM) and stirred, 1.61 ml of 10-times concentrated PBS was added and stirred to obtain a dispersion. The amount of the liquid (pure water, the aqueous phosphoric acid solution, NaOH, PBS) added was 95% by volume of the fibrous apatite/collagen composite dispersion.

The dispersion was introduced into a polystyrene-made, cylindrical molding die of 1.5 cm in inner diameter and 3.5 cm in height, and kept at 37° C. for 2 hours to obtain a jelly-like formed body (a). With a temperature sensor inserted into a center of this formed body (a), the formed body was placed in a freezer set at −80° C. The solidification temperature of the formed body (a) was −5° C. to −1° C., and the solidification time was 350 seconds. The resultant solidified body was dried in a vacuum oven (0° C. to 240° C., 760 to 1 Torr), and subjected to thermal dehydration and cross-linking under a reduced pressure of 1.33 hPa and at 140° C., to obtain a porous body (a-1) containing a fibrous apatite/collagen composite.

Figure 4:
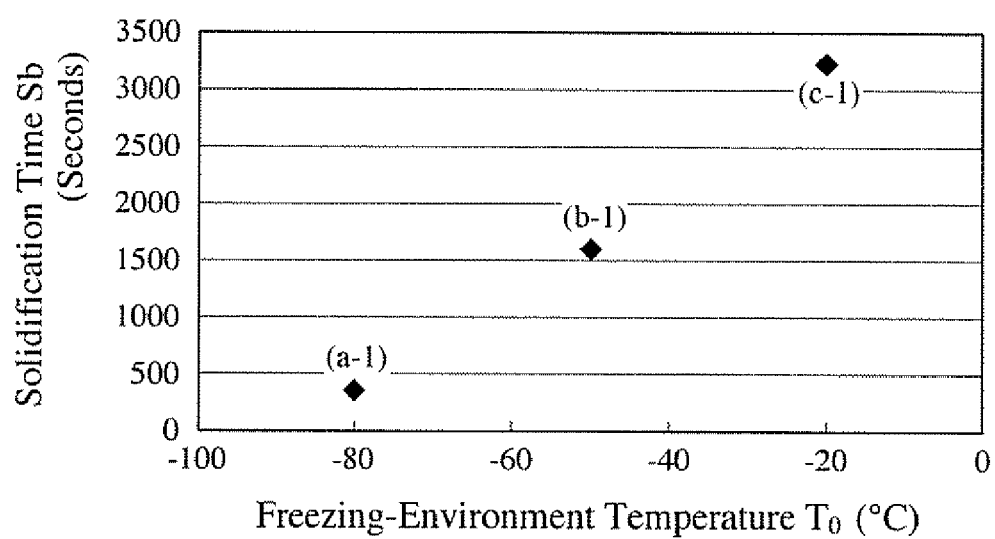
FIG. 4 is a graph showing the relation between gel solidification time and freezing-environment temperature in porous bodies (a-1), (b-1) and (c-1) each containing a fibrous apatite/collagen composite.

(3) Production of Porous Bodies (b-1) and (c-1) Each Containing Fibrous Apatite/Collagen Composite Porous bodies (b-1) and (c-1) each containing a fibrous apatite/collagen composite were produced in the same manner as in the steps (1) and (2) in Example 1, except that each formed body (b) and (c) having the same shape and composition as those of the jelly-like formed body (a) was placed in a freezer set at −50° C. and −20° C., respectively. The solidification time was 1609 seconds in the formed body (b) and 3240 seconds in the formed body (c). The solidification temperature was −5° C. to −1° C. in both bodies. Any porous body (a-1), (b-1) and (c-1) had a porosity of about 95%. FIG. 4 shows the relation between the freezing-environment temperatures $T_0$ (temperatures in the freezer) and their solidification time Sb in the porous bodies (a-1), (b-1) and (c-1). The solidification time Sb was substantially proportional to the freezing-environment temperature $T_0$.

(4) Measurement of Average Pore Diameter

Figure 5A:
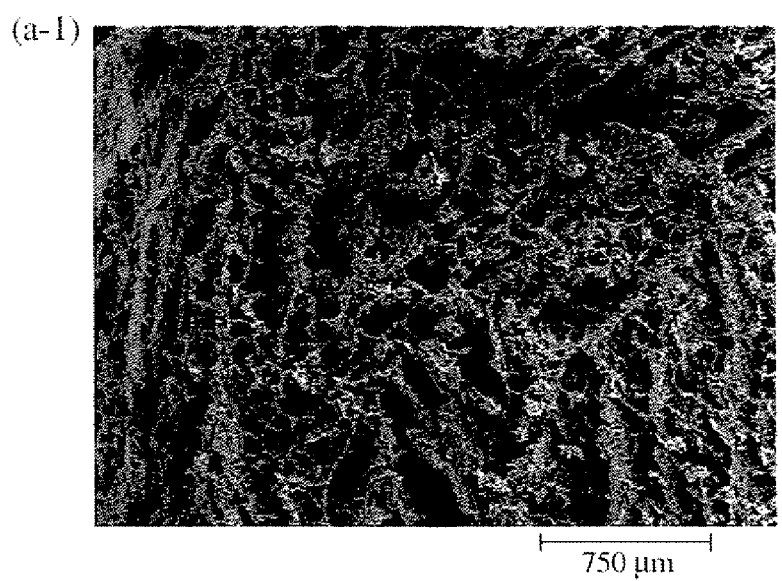
FIG. 5(a) is a scanning electron photomicrograph showing the porous body (a-1) containing a fibrous apatite/collagen composite.
Figure 5B:
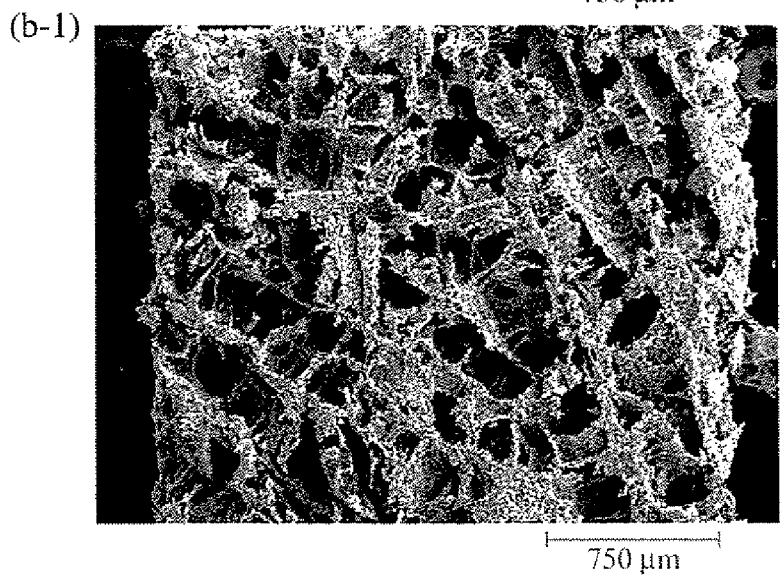
FIG. 5(b) is a scanning electron photomicrograph showing the porous body (b-1) containing a fibrous apatite/collagen composite.
Figure 5C:
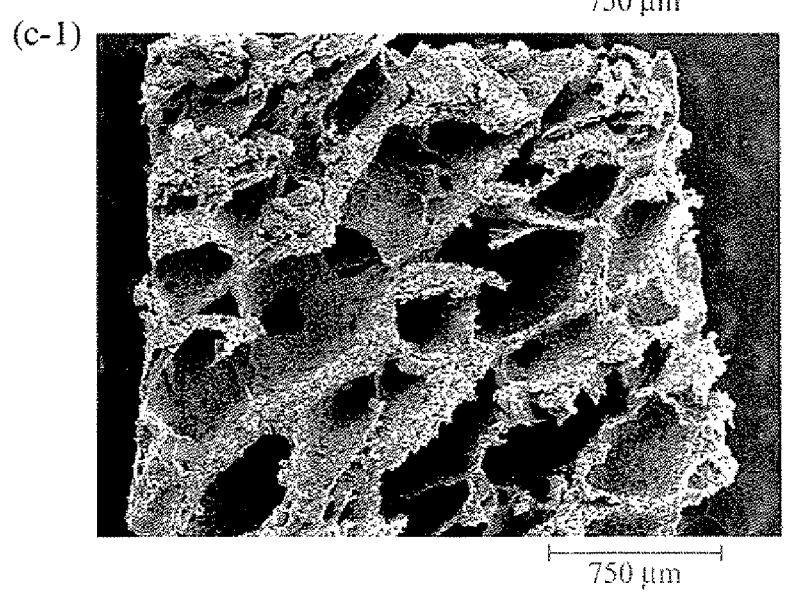
FIG. 5(c) is a scanning electron photomicrograph showing the porous body (c-1) containing a fibrous apatite/collagen composite.

The scanning electron photomicrographs of the cross sections of the porous bodies (a-1), (b-1) and (c-1) each containing a fibrous apatite/collagen composite are shown in FIG. 5. The average pore diameter of each porous body was measured by a line-intercept method. The results are shown in Table 1. Incidentally, diameter measurement was conducted on pores about 7 mm separate from the temperature sensor. The shorter the solidification time, the smaller the average pore diameter, and vice versa.

TABLE 1

| Porous Body | Freezing-Environment Temperature $T_0$ (° C.) | Solidification Time Sb (seconds) | Average Pore Diameter | |
|---|---|---|---|---|
| | | | (µm) | Standard Deviation |
| (a-1) | −80 | 350 | 93 | 53 |
| (b-1) | −50 | 1609 | 181 | 92 |
| (c-1) | −20 | 3240 | 378 | 142 |

EXAMPLE 2

Porous bodies (a-2), (b-2) and (c-2) each containing a fibrous apatite/collagen composite were produced in the same manner as in the steps (1)-(3) in Example 1, except for changing the formulation of the starting materials as shown in Table 2. Any porous body had a solidification temperature of −5° C. to −1° C.

TABLE 2

| No. | Fibrous Apatite/Collagen Composite | Water | 1-N NaOH Solution | Aqueous Collagen/Phosphoric Acid Solution | PBS | Liquid[1] |
|---|---|---|---|---|---|---|
| Example 1 | 2 g | 4.84 ml | 0.06 ml | 2 g | 1.61 ml | 95 vol. % |
| Example 2 | 4 g | 9.86 ml | 0.12 ml | 4 g | 1.529 ml | 90 vol. % |

Note:
[1]The amount of the liquid on a volume basis represents the total amount of pure water, the aqueous phosphoric acid solution, the aqueous NaOH solution and PBS per the dispersion containing a fibrous apatite/collagen composite.

Figure 6:
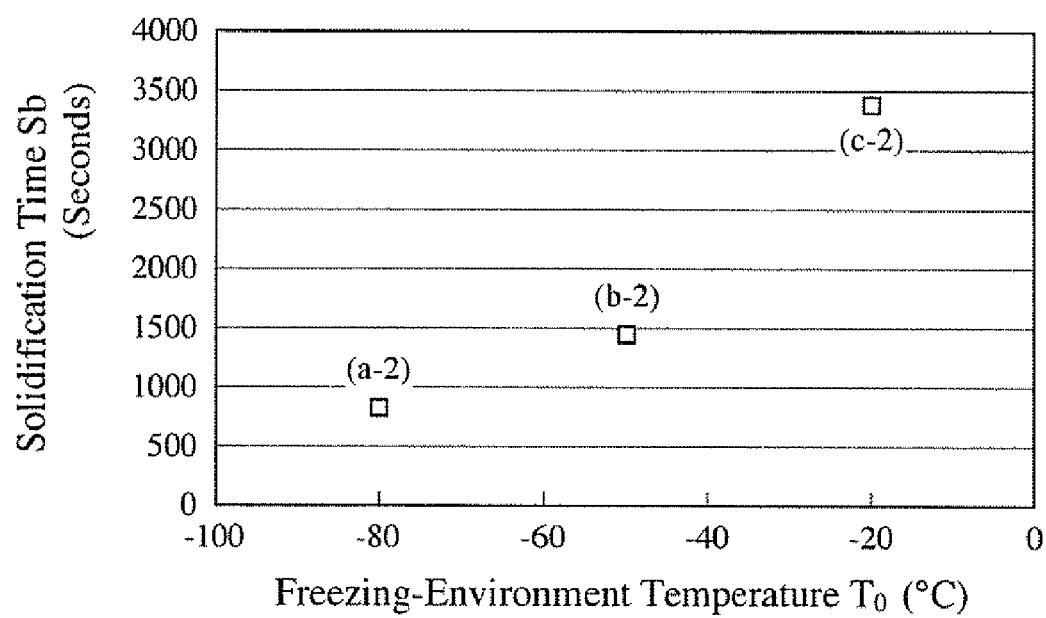
FIG. 6 is a graph showing the relation between gel solidification time and freezing-environment temperature in porous bodies (a-2), (b-2) and (c-2) each containing a fibrous apatite/collagen composite and freezing-environment temperatures.

FIG. 6 shows the relation between the freezing-environment temperature $T_0$ (temperature in the freezer) and the solidification time Sb in the porous bodies (a-2), (b-2) and (c-2). As in Example 1, the solidification time Sb was substantially proportional to the freezing-environment temperature $T_0$.

Figure 7A:
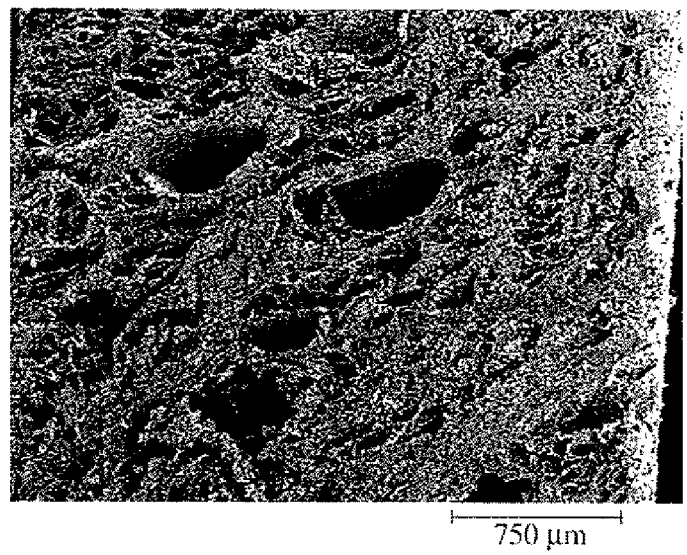
FIG. 7(a) is a scanning electron photomicrograph showing the porous body (a-2) containing a fibrous apatite/collagen composite.
Figure 7B:
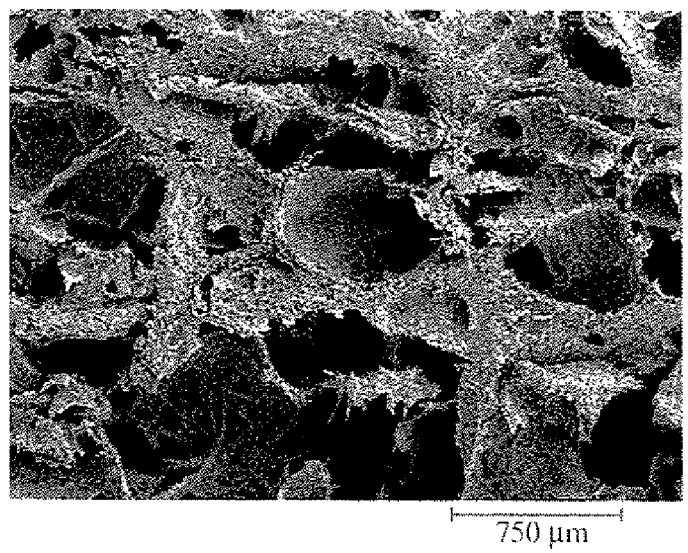
FIG. 7(b) is a scanning electron photomicrograph showing the porous body (b-2) containing a fibrous apatite/collagen composite.
Figure 7C:
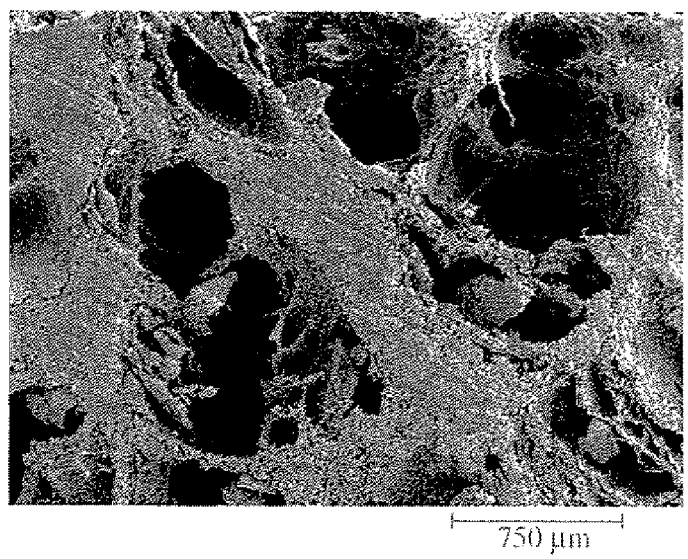
FIG. 7(c) is a scanning electron photomicrograph showing the porous body (c-2) containing a fibrous apatite/collagen composite.

The scanning electron photomicrographs of the cross sections of the porous bodies (a-2), (b-2) and (c-2) are shown in FIG. 7. FIG. 7 indicates that the porous bodies (a-2), (b-2) and (c-2) having a porosity of 90% were thicker in walls than those having a porosity of 95% (Example 1). The average pore diameter of each porous body was measured by a line-intercept method. The results are shown in Table 3 below.

TABLE 3

| Porous Body | Freezing-Environment Temperature $T_0$ (° C.) | Solidification Time Sb (seconds) | Average Pore Diameter | |
|---|---|---|---|---|
| | | | (µm) | Standard Deviation |
| (a-2) | −80 | 835 | 97 | 71 |
| (b-2) | −50 | 1439 | 330 | 150 |
| (c-2) | −20 | 3388 | 619 | 411 |

Figure 8:
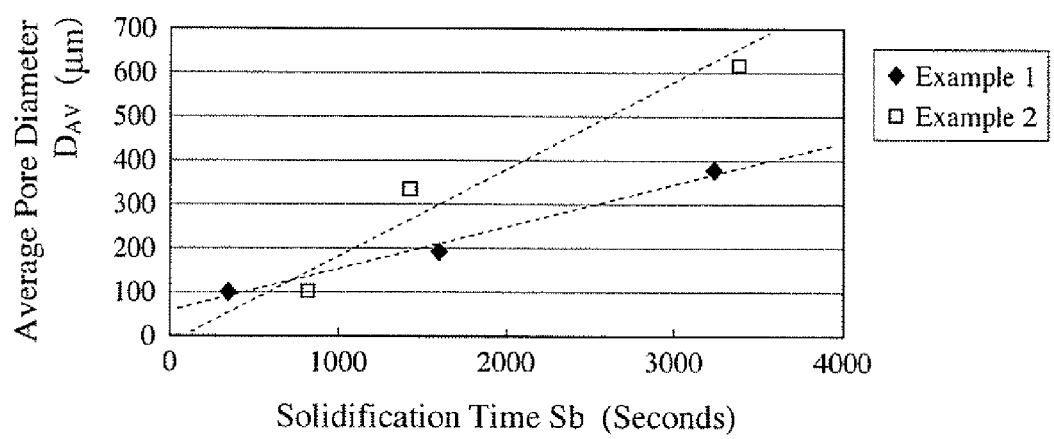
FIG. 8 is a graph showing the relation between the solidification time and the average pore diameter.

FIG. 8 shows the relation between the solidification time Sb and the average pore diameter $D_{AV}$ in the porous bodies of Examples 1 and 2. The average pore diameter of the porous body containing a fibrous apatite/collagen composite was substantially proportional to the solidification time Sb of the formed body. Also, the inclination of a line of the average pore diameter relative to the solidification time Sb is larger in the porosity of 90% (Example 2) than in the porosity of 95% (Example 1). This is due to the fact that as long as the solidification time is the same, the smaller the amount of the solidifying water, the longer the ice crystal growth time, and thus the larger diameter each ice-containing pore has. Using the graphs shown in FIGS. 4, 6 and 8, porous bodies having desired average pore diameters were able to be produced.

EFFECT OF THE INVENTION

The method of the present invention controls the average pore diameter of an apatite/collagen porous body by the time for solidifying a gel of a dispersion comprising a fibrous apatite/collagen composite, collagen and water. Because the solidification time depends on the temperature of an environment in which the gel is kept for freezing (freezing-environment temperature) the determination of the relation between the solidification time and the freezing-environment temperature makes it possible to provide an apatite/collagen porous body with a desired average pore diameter simply by solidifying a gel at a predetermined temperature. This method is extremely simple because it can control the average pore diameter of the product only by a freezing-environment temperature.

The average pore diameter of the apatite/collagen porous body has influence on the mechanical strength and biocompatibility of the resultant porous body. Accordingly, the method of the present invention capable of producing the apatite/collagen porous body having a desired average pore diameter is useful to produce porous bodies for artificial bone, cell scaffolds, etc.

What is claimed is:

1. A method for controlling an average pore diameter of a porous body comprising a fibrous apatite/collagen composite, said porous body being produced by:

gelating a dispersion comprising said fibrous apatite/collagen composite, collagen and water;

freeze-drying the resultant gel to form a porous body; and cross-linking the collagen in said porous body, wherein the average pore diameter of the porous body is controlled by the following in the following order:

a) freezing pluralities of gels at various freezing-environment temperatures and measuring the solidification time of each gel to prepare a graph showing the relation between the freezing-environment temperature and the solidification time;

b) measuring the average pore diameter of the porous body obtained at various lengths of solidification time to prepare a graph showing the relation between solidification time and average pore diameter;

c) determining the solidification time for providing a desired average pore diameter of said porous body from the graph of the solidification time and the average pore diameter; and d) determining the freezing-environment temperature for achieving the determined solidification time from the graph of the freezing-environment temperature and the solidification time.

2. The method for controlling the average pore diameter according to claim 1, wherein the temperature for keeping said gel for freezing is −100° C. to 0° C.

* * * * *